US008581150B1

(12) United States Patent
Greif

(10) Patent No.: US 8,581,150 B1
(45) Date of Patent: Nov. 12, 2013

(54) PORTABLE WARMER FOR USE WITH CELL CULTURE PLATE

(76) Inventor: Charlotte Swann Greif, San Antonio, TX (US)

( * ) Notice: Subject to any disclaimer, the term of this patent is extended or adjusted under 35 U.S.C. 154(b) by 130 days.

(21) Appl. No.: 13/156,843

(22) Filed: Jun. 9, 2011

(51) Int. Cl.
*F24C 7/10* (2006.01)
*C12Q 1/02* (2006.01)

(52) U.S. Cl.
USPC ............. 219/386; 219/385; 219/387; 435/29; 435/303.1; 435/297.1; 435/383

(58) Field of Classification Search
USPC .............. 219/385–387; 435/29, 303.1, 297.1, 435/383
See application file for complete search history.

(56) References Cited

U.S. PATENT DOCUMENTS

2009/0098593 A1 * 4/2009 Ehrhardt et al. ................ 435/29

* cited by examiner

*Primary Examiner* — Shawntina Fuqua
(74) *Attorney, Agent, or Firm* — Wayne J. Colton, Inc.

(57) ABSTRACT

A portable warmer for use with a cell culture plate in order to maintain culture samples borne by the culture plate at a desired temperature includes a body having formed therein a shelf that is sized and shaped to generally conform to the outside dimensions of the base of a cell culture plate. The shelf includes a substantially horizontal surface atop of which the base of the cell culture plate may be freely rested. The shelf also includes a preferably electric heating element, which may be formed unitary with the horizontal surface of the shelf or may be contained within the body of the portable warmer in an area and in a manner adapted to cause heating of the horizontal surface of the shelf. The portable warmer is provided with one or more clamping devices for securing a received cell culture plate in place atop the shelf.

12 Claims, 3 Drawing Sheets

PORTABLE WARMER FOR USE WITH CELL CULTURE PLATE

FIELD OF THE INVENTION

The present invention relates to laboratory sciences. More particularly, the invention relates to a portable warmer for use with a cell culture plate in order to maintain culture samples borne by the culture plate at a desired temperature.

BACKGROUND OF THE INVENTION

Numerous laboratory conducted cell-based assays ranging from cell growth, seeding, cell feeding and washing to in-plate differentiation of pluropotential stem cells rely on the use of a cell culture plate for containing multiple independent culture specimens during manipulation. As shown in FIG. 1, a typical cell culture plate 30 simply comprises a plurality of individual specimen wells 31 arranged and dependently supported atop a unitary base 32. While normally stored within an incubator or other temperature controlled environment—typically at or about a temperature of 37° C., the cell culture plate 30 and its contents must generally be removed from such a temperature controlled environment in order that a scientist or other laboratory worker may analyze or manipulate the specimens carried by the cell culture plate 30.

Although the foregoing procedure is generally adequate for work conducted by experienced laboratory personnel working with robust specimens, it is found by Applicant to be inadequate under at least a number of circumstances. In one example, it is noted that some cellular tissues, including in particular, pluropotential stem cells, are quite sensitive to temperature deviations, where for exposure for even a short duration to typical room temperature may be expected to cause cellular degradation and possibly mortality. While in many cases this operating parameter may enable an experienced laboratory worker to successfully conduct a required task, it is also noted that such cells as pluropotential stem cells are very difficult to obtain and, consequently, are very valuable. As a result, it would be to the benefit of even experienced laboratory personnel to have available a method and apparatus for maintaining such tissue specimens at a desired temperature during analysis or manipulation.

In a further example applicable to many types of living specimens, it is noted that student scientists are very often unable to complete an analysis, experiment or manipulation in the short period of time that a tissue sample remains viable outside of incubation. In these cases, the learning process can quickly become frustrating as the motivation of success is repeatedly taken away or errors in laboratory procedures are created by the need to rush through an experiment. Still further, however, it is noted that even in situations where students have attained the laboratory skills required to work quickly, the limited viability time is an impossible constraint on the instructor, preventing individual work with students for fear that in the time that it takes to help one student an entire classroom of experiments may be lost.

With the forgoing disadvantages of the prior art clearly in mind, it is therefore an overriding object of the present invention to provide a method and apparatus by which tissue samples may be analyzed or manipulated outside of an incubator or otherwise temperature controlled general environment with eliminated or reduced risk for temperature related cell death. Additionally, it is an object of the present invention to provide such a method and apparatus that is inexpensive to implement and simple to use, thereby making such a method and apparatus generally available for use across the full spectrum of laboratory environments from fully funded research facilities to minimally supported school programs.

SUMMARY OF THE INVENTION

In accordance with the foregoing objects, the present invention—a portable warmer for use with a cell culture plate in order to maintain culture samples borne by the culture plate at a desired temperature—generally comprises a body having formed therein a shelf that is sized and shaped to generally conform to the outside dimensions of the base of a cell culture plate. The shelf includes a substantially horizontal surface atop of which the base of the cell culture plate may be freely rested. Additionally, the shelf also includes a preferably electric heating element, which may be formed unitary with the horizontal surface of the shelf or may be contained within the body of the portable warmer in an area and in a manner adapted to cause heating of the horizontal surface of the shelf. Still further, the portable warmer is provided with one or more clamping devices or the substantial equivalent thereof for securing a received cell culture plate in place atop the shelf.

In use, a cell culture plate is utilized as is otherwise conventional to contain one or more tissue specimens. With the tissue specimens carried by the cell culture plate, the cell culture plate is mated with the portable warmer by placing the base of the cell culture plate atop the horizontal surface of the shelf of the portable warmer. In order to prevent accidental dislodgment from the shelf of the cell culture plate, one or more provided clamping devices (or the substantial equivalent thereof) are operated to secure the cell culture plate in place. An ON-OFF switch and temperature control are then conventionally utilized in combination with a temperature to generate with the portable warmer the desired temperature, which desired temperature will depend upon the composition of the tissue sample or tissue samples. The appropriate temperature thus being generated by the portable warmer, the heat is then conducted from the portable warmer to the cell culture plate, thereby applying heat to any tissue specimen carried by the cell culture plate.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 2:
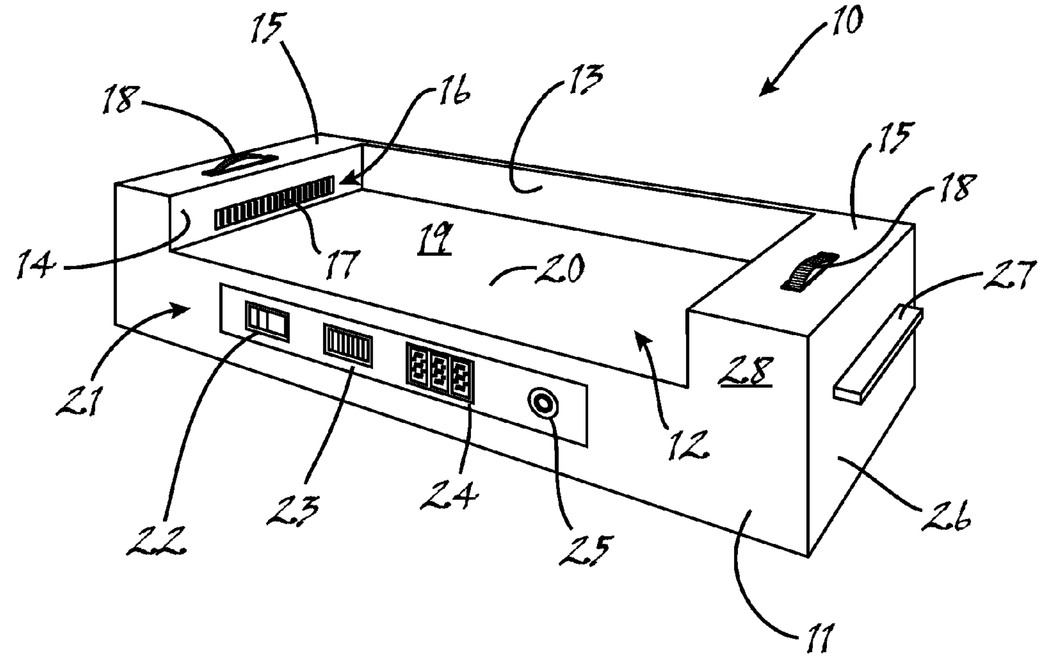
FIG. 2 shows, in a perspective view, a preferred embodiment of a portable warmer as particularly suited for use in connection with a cell culture plate such as that shown in FIG. 1.
Figure 3:
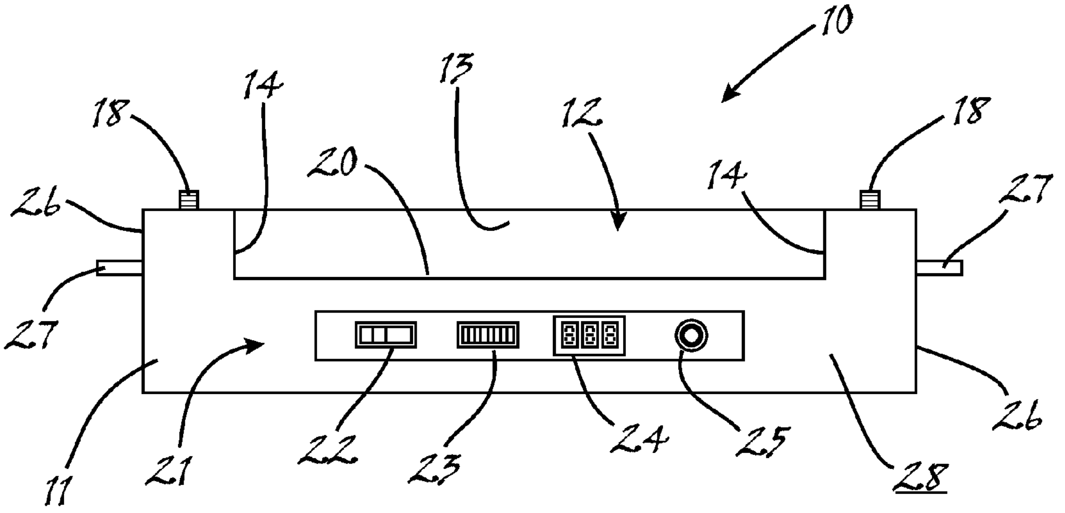
FIG. 3 shows, in a front elevational view, various details, including, in particular, details of the preferred controls, of the portable warmer of FIG. 2.
Figure 4:
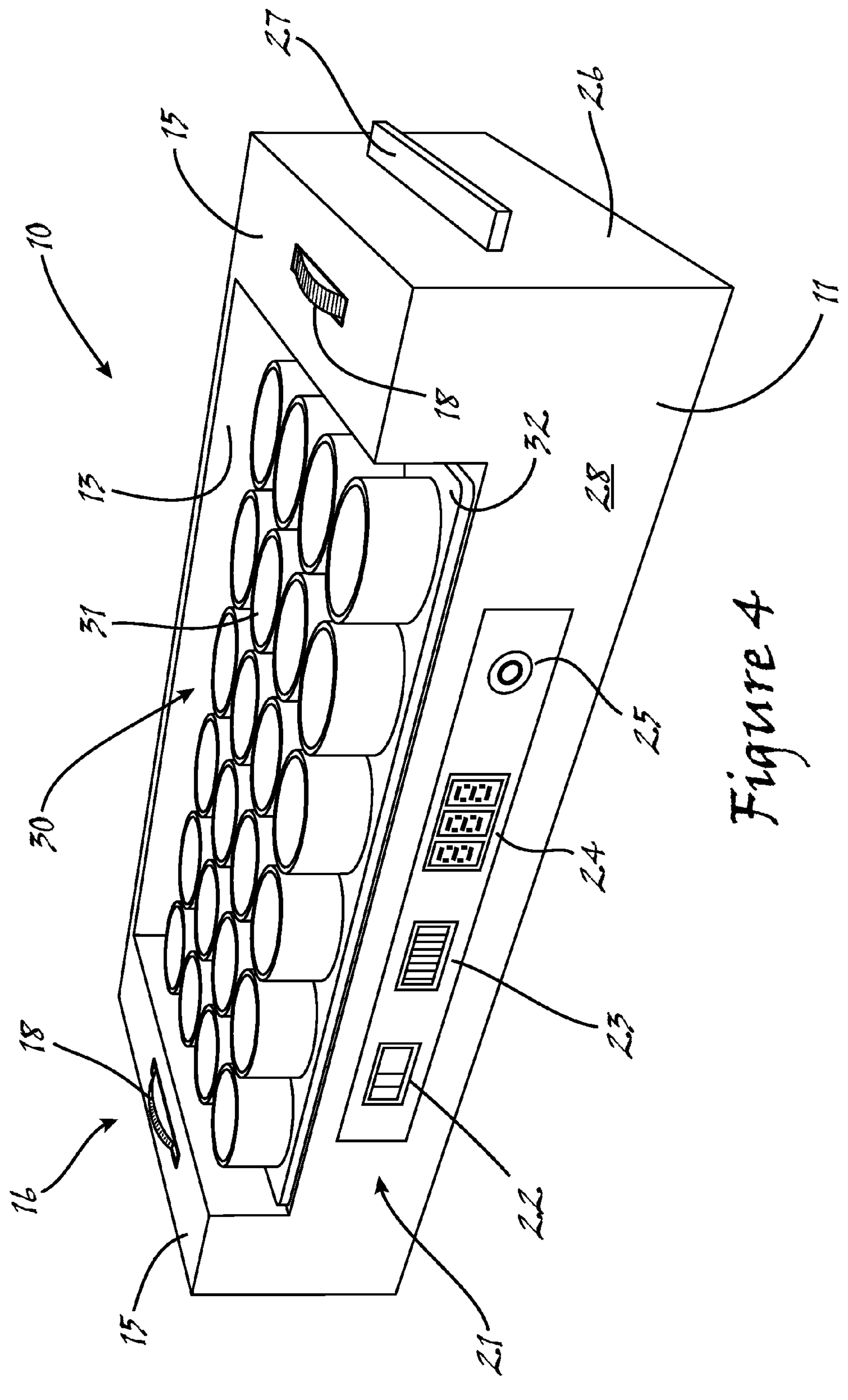
FIG. 4 shows, in a perspective view, the portable warmer of FIG. 2 as employed for use with the cell culture plate of FIG. 1.

Referring now to the Figures, and to FIGS. 2 and 3 in particular, the preferred implementation of the portable warmer 10 of the present invention is shown to generally comprise a body 11 having formed therein a shelf 12 sized and shaped to generally conform to the outside dimensions of the base 32 of a cell culture plate 30. As shown in the Figures, the shelf 12 comprises a substantially horizontal surface 19 atop of which the base 32 of the cell culture plate 30 may be freely rested. As will be better appreciated further herein, the shelf 12 also comprises a preferably electric heating element 20, which heating element may be formed unitary with the horizontal surface 19 of the shelf 12 or may be contained within the body 11 of the portable warmer in an area and in a manner adapted to cause heating of the horizontal surface 19 of the shelf 12.

In the most preferred implementation of the portable warmer 10 of the present invention, the shelf 12 is formed within the body 11 by providing in the body a back wall 13 and two side walls 14. In this manner, a cell culture plate 30 may readily be positioned atop the shelf for use of the portable warmer 10 during the conduct of laboratory work. As also shown in the figures, however, the portable warmer 10 of the present invention is also most preferably provided with one or more clamping devices 16 in order to secure a cell culture plate 30 firmly in place atop the shelf 12 of the portable warmer 10.

As particularly shown in FIG. 2, such a clamping device 16 may be implemented by the provision about one or both side walls 14 of a preferably cushioned bumper 17 operable to engage a supported cell culture plate 30 in the manner of a vise. In at least one implementation, a provided bumper 17 is conventionally journaled to a threaded shaft extending through a matingly threaded orifice through the center of a thumbwheel 18 dependently partially recessed beneath the top surface 15 of the side wall 14. As will be appreciated by those of ordinary skill in the art, turning the recessed thumbwheel in one direction will cause the bumper 17 to move toward and into securing engagement with the cell culture plate 30 while turning the thumbwheel in the opposite direction with cause the bumper 17 to retract back into the sidewall 14 away from the cell culture plate 30, thereby releasing its clamping grip on the cell culture plate 30.

As particularly shown in FIGS. 2 and 3, appropriate controls 21 for operation and/or monitoring of the operation of the portable warmer 10 are conveniently provided on the front face 28 of the body 11 of the portable warmer 10. Although more or fewer controls may be provided in any particular implementation within the scope of the present invention, the preferred implementation of the present invention comprises at least an ON-OFF switch 22 and a temperature indicator 24. Although the portable warmer 10 may be permanently set to deliver a particular level of heat, such as, for example, 37° C., the most preferred implementation of the portable warmer also includes the provision of a temperature adjustment 23, in which case the temperature indicator 24 is also preferably adapted to report both the heat setting and the actual produced temperature. In any case, the portable warmer 10 also preferably includes a power connector 25 for providing external electrical power to the heating element 20.

Figure 1:
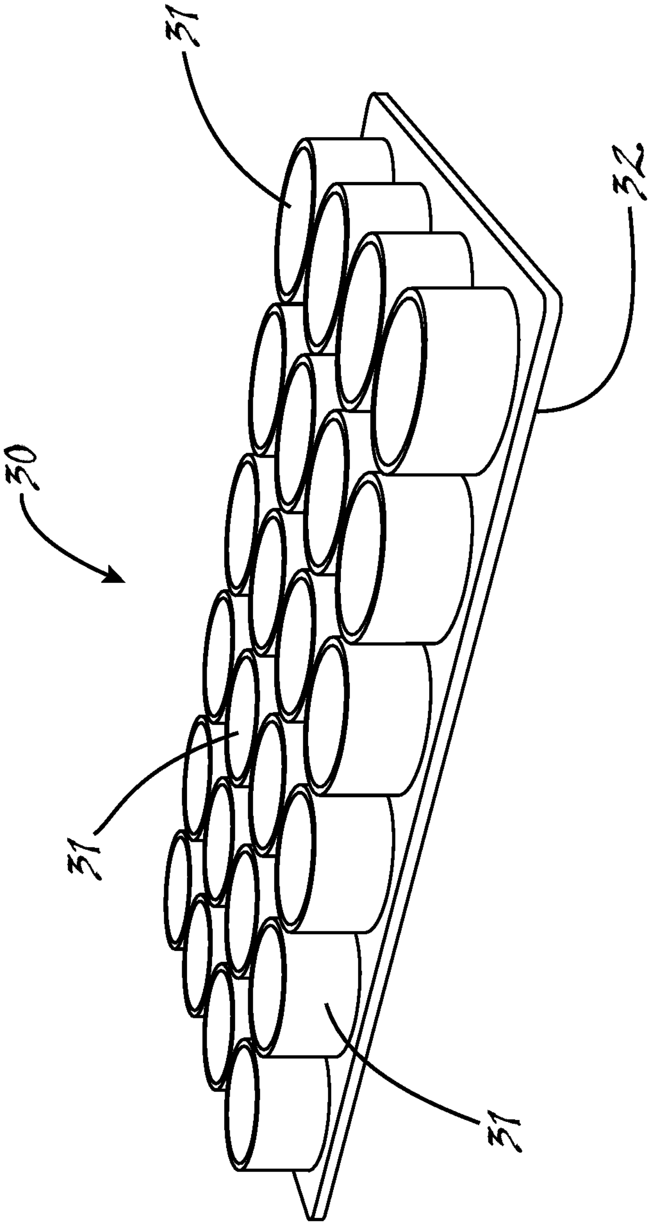
Figure 1 (Prior Art)
FIG. 1 shows, in a perspective view, a cell culture plate as is typically representative of the prior art.

For use of the portable warmer 10 of the present invention, a cell culture plate such as the multi-well cell culture plate 30 depicted in FIG. 1 is utilized as is otherwise conventional to contain one or more tissue specimens. With the tissue specimens carried by the cell culture plate 30, the cell culture plate 30 is mated with the portable warmer 10 by placing the base 32 of the cell culture plate atop the horizontal surface 19 of the shelf 12 of the portable warmer 10. In order to prevent accidental dislodgment from the shelf 12 of the cell culture plate 30, one or more provided clamping devices 16 are used (as previously described in detail) to secure the cell culture plate 30 in place. The ON-OFF switch 22 and temperature control 23 are then conventionally utilized, in combination with the monitoring of the temperature indicator 24 if present, to generate with the portable warmer 10 the desired temperature, which temperature will depend upon the composition of the tissue sample or tissue samples as is well known to those of ordinary skill in the art. The appropriate temperature thus being generated by the portable warmer 10, the heat is then conducted from the portable warmer 10 to the cell culture plate, thereby applying heat to the one or more tissue specimens carried in the one or more specimen wells 31 of the cell culture plate 30.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, the present invention also contemplates that the heating element 25 may be operated for at least some period of time from one or more preferably rechargeable batteries provided interior the body 11 of the portable warmer 10. To this end, a charging circuit for the batteries, implemented as otherwise is conventional, is interposed the provided power input 25 and the provided battery or batteries.

Likewise, as particularly shown in FIGS. 2 and 3, those of ordinary skill in the art will recognize in light of this exemplary description that a plurality of handles 27 are desirably provided for ensuring that a good grip may be had while transporting the portable warmer 10 from one location to another. As shown in the figures, such handles may be readily affixed to the sides 26 of the body 11 of the portable warmer 10 or at any other convenient location. In any case, because the scope of the present invention is much broader than any particular embodiment, the foregoing detailed description should not be construed as a limitation of the scope of the present invention, which is limited only by the claims appended hereto.

What is claimed is:

1. A portable warmer for use in connection with a cell culture plate, said portable warmer comprising:

a body having formed therein a shelf, said shelf being sized and shaped to dependently receive thereon the cell culture plate;

a heating element associated with said shelf within said body, said heating element being adapted to provide heat through said shelf to a cell culture plate dependently received by said shelf;

means for securing a cell culture plate atop said shelf; and wherein:

said heating element comprises an electric heating element; and said means for securing a cell culture plate atop said shelf comprises a clamping device.

2. The portable warmer for use in connection with a cell culture plate as recited in claim 1, wherein said means for securing a cell culture plate atop said shelf comprises a plurality of clamping devices.

3. The portable warmer for use in connection with a cell culture plate as recited in claim 1, wherein said clamping device is operated with a thumbwheel.

4. The portable warmer for use in connection with a cell culture plate as recited in claim 1, wherein said heating element is battery powered.

5. The portable warmer for use in connection with a cell culture plate as recited in claim 4, wherein said heating element is additionally externally powered.

6. The portable warmer for use in connection with a cell culture plate as recited in claim 5, said portable warmer further comprising an ON-OFF switch.

7. The portable warmer for use in connection with a cell culture plate as recited in claim 6, said portable warmer further comprising a temperature control.

8. The portable warmer for use in connection with a cell culture plate as recited in claim 7, said portable warmer further comprising a temperature indicator.

9. The portable warmer for use in connection with a cell culture plate as recited in claim 1, wherein said heating element is externally powered.

10. The portable warmer for use in connection with a cell culture plate as recited in claim 9, said portable warmer further comprising an ON-OFF switch.

11. The portable warmer for use in connection with a cell culture plate as recited in claim 10, said portable warmer further comprising a temperature control.

12. The portable warmer for use in connection with a cell culture plate as recited in claim 11, said portable warmer further comprising a temperature indicator.

* * * * *